(12) United States Patent
Phillips

(10) Patent No.: US 7,601,169 B2
(45) Date of Patent: Oct. 13, 2009

(54) ACCOMMODATING INTRAOCULAR LENS

(76) Inventor: Andrew F. Phillips, 3579 E. Foothill #246, Pasadena, CA (US) 91107

( * ) Notice: Subject to any disclaimer, the term of this patent is extended or adjusted under 35 U.S.C. 154(b) by 57 days.

(21) Appl. No.: 11/562,035

(22) Filed: Nov. 21, 2006

(65) Prior Publication Data

US 2007/0142913 A1    Jun. 21, 2007

Related U.S. Application Data

(63) Continuation of application No. 10/886,847, filed on Jul. 8, 2004, now Pat. No. 7,503,938, which is a continuation-in-part of application No. 10/189,992, filed on Jul. 5, 2002, now abandoned, which is a continuation-in-part of application No. 10/090,675, filed on Mar. 5, 2002, now abandoned.

(51) Int. Cl.
*A61F 2/16* (2006.01)

(52) U.S. Cl. ..................... 623/6.18; 623/6.45

(58) Field of Classification Search ............... 623/6.12, 623/6.13, 6.18, 6.22, 6.45, 6.37, 6.39, 6.32, 623/6.34
See application file for complete search history.

(56) References Cited

U.S. PATENT DOCUMENTS

| | | | |
|---|---|---|---|
| 4,304,012 A * | 12/1981 | Richard | 623/6.51 |
| 4,373,218 A | 2/1983 | Schachar | |
| 4,409,691 A | 10/1983 | Levy | |
| 4,463,457 A * | 8/1984 | Kelman | 623/6.43 |
| 4,527,294 A * | 7/1985 | Heslin | 623/6.12 |
| 4,534,069 A | 8/1985 | Kelman | |
| 4,575,373 A | 3/1986 | Johnson | |
| 4,575,878 A * | 3/1986 | Dubroff | 623/6.53 |
| 4,586,930 A * | 5/1986 | Kelman | 623/6.45 |
| 4,666,446 A | 5/1987 | Koziol et al. | |
| 4,685,922 A | 8/1987 | Peyman | |
| 4,693,717 A | 9/1987 | Michelson | |
| 4,718,904 A | 1/1988 | Thornton | |
| 4,781,719 A | 11/1988 | Kelman | |
| 4,842,601 A | 6/1989 | Smith | |
| 4,888,012 A | 12/1989 | Horn et al. | |
| 4,888,015 A | 12/1989 | Domino | |
| 4,892,543 A | 1/1990 | Turley | |
| 4,932,966 A | 6/1990 | Christie et al. | |

(Continued)

OTHER PUBLICATIONS

Downloaded from Internet: "Multifocal vs. Monofocal: the ARRAY Difference", 4 pages, at www.arraylens.com/array/multifocal.html.

*Primary Examiner*—Corrine McDermott
*Assistant Examiner*—Cheryl Miller
(74) *Attorney, Agent, or Firm*—Gordon & Jacobson, PC

(57) ABSTRACT

An intraocular lens (IOL) system includes an optic, a pair of haptics located on sides of the optic, and hinge portions at each of the optic haptic junctions. The hinge portions have stressed and non-stressed configurations. One or more restraining elements are provided to maintain the stressed state configuration of the hinge portion during implantation and during a post-operative period during which the capsular bag of the eye heals about the lens. The restraining elements are thereafter removable, preferably via a non-surgically invasive manner, e.g., via dissolution or laser light. Removal of the restraining elements allows anteriorization of the optic as the lens assumes a non-stressed configuration during accommodation. The ciliary body and lens may then interact in a manner substantially similar to the physiological interaction between the ciliary body and a healthy natural crystalline lens.

23 Claims, 13 Drawing Sheets

U.S. PATENT DOCUMENTS

| | | | |
|---|---|---|---|
| 4,944,082 A | | 7/1990 | Jones et al. |
| 5,026,393 A | * | 6/1991 | Mackool ..................... 606/107 |
| 5,108,429 A | | 4/1992 | Wiley |
| 5,282,851 A | | 2/1994 | Jacob-LaBarre |
| 5,288,293 A | | 2/1994 | O'Donnell, Jr. |
| 5,376,115 A | * | 12/1994 | Jansen ....................... 623/6.49 |
| 5,476,514 A | | 12/1995 | Cumming |
| 5,496,366 A | | 3/1996 | Cumming |
| 5,549,668 A | | 8/1996 | O'Donnell, Jr. |
| 5,571,177 A | | 11/1996 | Deacon et al. |
| 5,607,472 A | * | 3/1997 | Thompson .................. 623/6.13 |
| 5,728,156 A | * | 3/1998 | Gupta et al. ............... 623/6.26 |
| 5,769,890 A | * | 6/1998 | McDonald .................. 623/6.34 |
| 6,027,531 A | | 2/2000 | Tassignon |
| 6,051,024 A | | 4/2000 | Cumming |
| 6,197,059 B1 | * | 3/2001 | Cumming .................. 623/6.39 |
| 6,200,342 B1 | | 3/2001 | Tassignon |
| 6,217,612 B1 | | 4/2001 | Woods |
| 6,231,603 B1 | | 5/2001 | Lang et al. |
| 6,261,321 B1 | | 7/2001 | Kellan |
| 6,299,641 B1 | | 10/2001 | Woods |
| 6,413,277 B1 | | 7/2002 | Neuhann |
| 6,443,984 B1 | | 9/2002 | Jahn et al. |
| 6,494,911 B2 | | 12/2002 | Cumming |
| 6,517,577 B1 | | 2/2003 | Callahan et al. |
| 6,660,035 B1 | * | 12/2003 | Lang et al. ................. 623/6.37 |
| 6,899,732 B2 | * | 5/2005 | Zadno-Azizi et al. ...... 623/6.33 |
| 7,018,410 B1 | | 3/2006 | Vazeen |
| 2002/0133228 A1 | | 9/2002 | Sarver |
| 2003/0060878 A1 | | 3/2003 | Shadduck |
| 2003/0135271 A1 | | 7/2003 | Bandhauer |
| 2003/0187504 A1 | | 10/2003 | Weinschenk et al. |

* cited by examiner

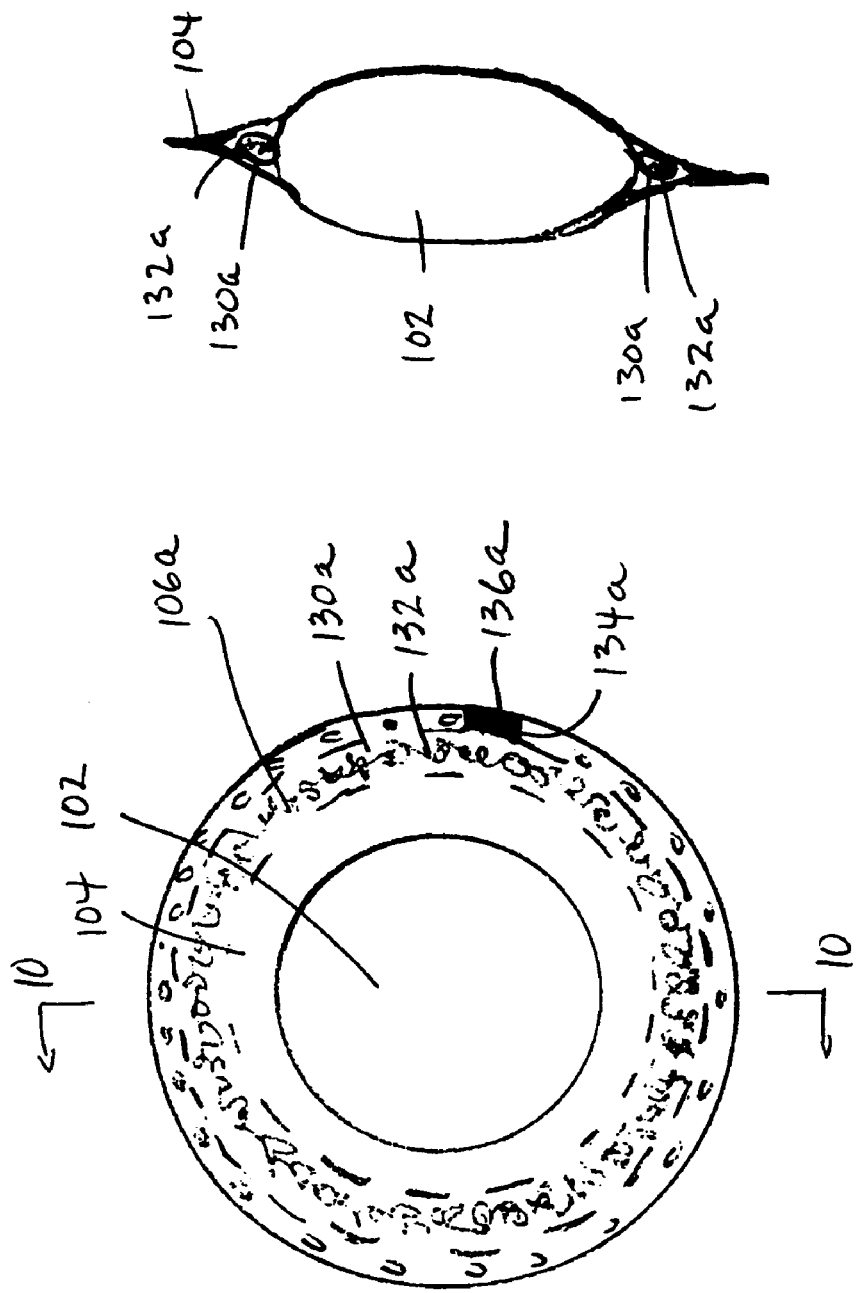

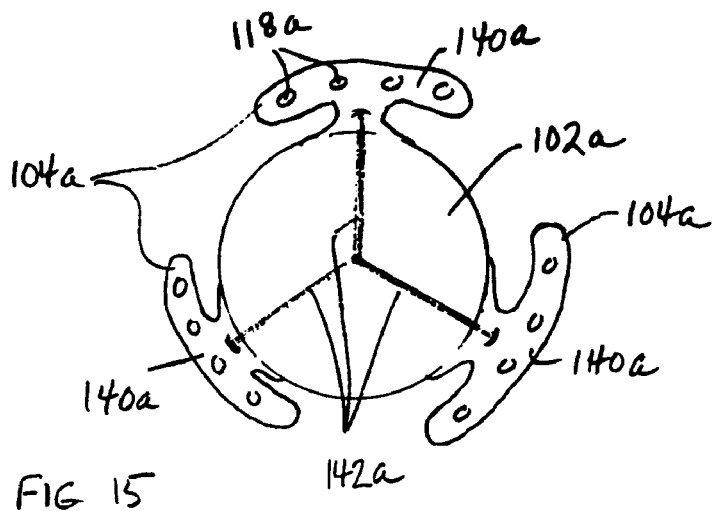
FIG. 15
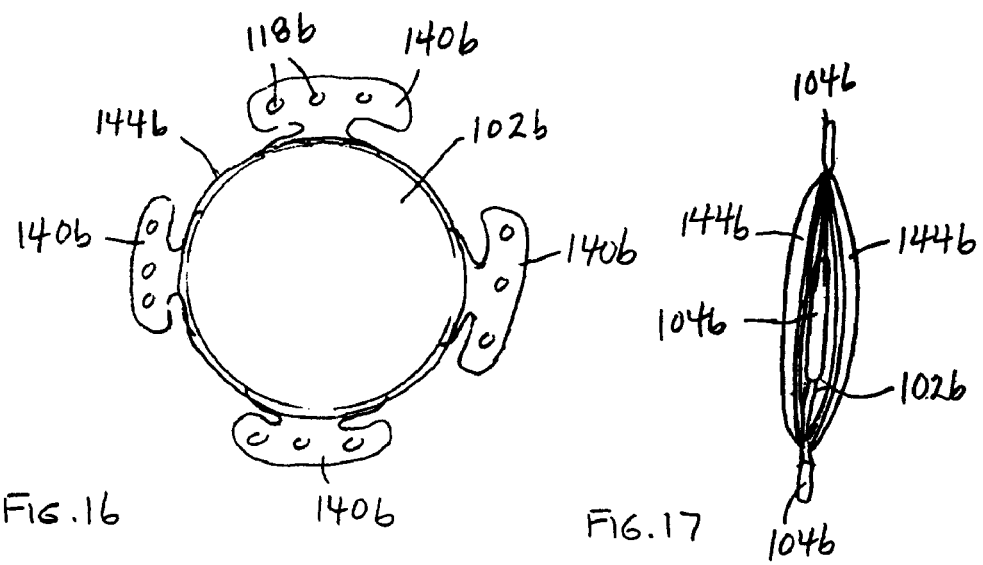
FIG. 16
FIG. 17
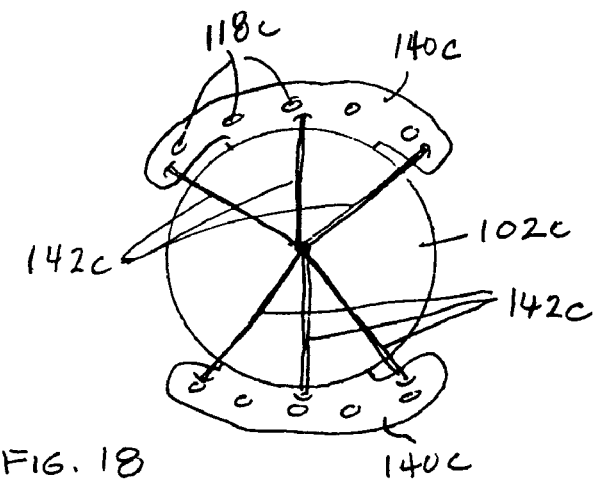
FIG. 18

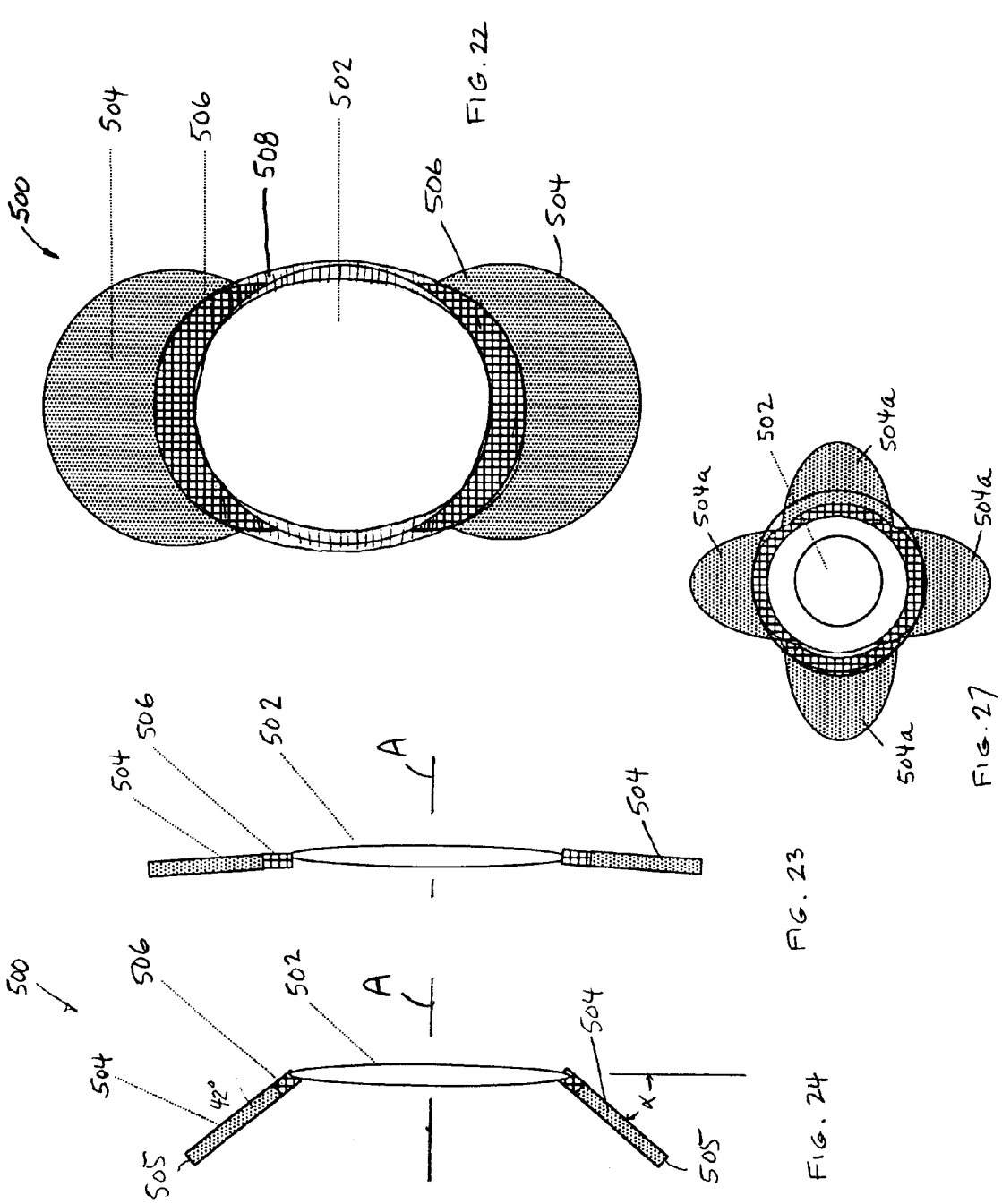

ACCOMMODATING INTRAOCULAR LENS

This application is a continuation of U.S. Ser. No. 10/886,847, now U.S. Pat. No. 7,503,938 filed Jul. 8, 2004, which is a continuation-in-part of U.S. Ser. No. 10/189,992, filed Jul. 5, 2002, now abandoned which is a continuation-in-part of U.S. Ser. No. 10/090,675, filed Mar. 5, 2002, now abandoned which are both incorporated by reference herein in their entireties.

BACKGROUND OF THE INVENTION

1. Field of the Invention

This invention relates broadly to ophthalmic implants. More particularly, this invention relates to intraocular lenses which are focusable and allow for accommodation for near vision.

2. State of the Art

Referring to FIG. 1, the human eye 10 generally comprises a cornea 12, an iris 14, a ciliary body (muscle) 16, a capsular bag 18 having an anterior wall 20 and a posterior wall 22, and a natural crystalline lens 24 contained with the walls of the capsular bag. The capsular bag 18 is connected to the ciliary body 16 by means of a plurality of zonules 26 which are strands or fibers. The ciliary body 16 surrounds the capsular bag 18 and lens 24, defining an open space, the diameter of which depends upon the state (relaxed or contracted) of the ciliary body 16.

When the ciliary body 16 relaxes, the diameter of the opening increases, and the zonules 26 are pulled taut and exert a tensile force on the anterior and posterior walls 20, 22 of the capsular bag 18, tending to flatten it. As a consequence, the lens 24 is also flattened, thereby undergoing a decrease in focusing power. This is the condition for normal distance viewing. Thus, the emmetropic human eye is naturally focused on distant objects.

Through a process termed accommodation, the human eye can increase its focusing power and bring into focus objects at near. Accommodation is enabled by a change in shape of the lens 24. More particularly, when the ciliary body 16 contracts, the diameter of the opening is decreased thereby causing a compensatory relaxation of the zonules 26. This in turn removes or decreases the tension on the capsular bag 18, and allows the lens 24 to assume a more rounded or spherical shape. This rounded shape increases the focal power of the lens such that the lens focuses on objects at near.

As such, the process of accommodation is made more efficient by the interplay between stresses in the ciliary body and the lens. When the ciliary body relaxes and reduces its internal stress, there is a compensatory transfer of this stress into the body of the lens, which is then stretched away from its globular relaxed state into a more stressed elongated conformation for distance viewing. The opposite happens as accommodation occurs for near vision, where the stress is transferred from the elongated lens into the contracted ciliary body.

In this sense, referring to FIG. 2, there is conservation of potential energy (as measured by the stress or level of excitation) between the ciliary body and the crystalline lens from the point of complete ciliary body relaxation for distance vision through a continuum of states leading to full accommodation of the lens.

As humans age, there is a general loss of ability to accommodate, termed "presbyopia", which eventually leaves the eye unable to focus on near objects. In addition, when cataract surgery is performed and the natural crystalline lens is replaced by an artificial intraocular lens, there is generally a complete loss of the ability to accommodate. This occurs because the active muscular process of accommodation involving the ciliary body is not translated into a change in focusing power of the implanted artificial intraocular lens.

There have been numerous attempts to achieve at least some useful degree of accommodation with an implanted intraocular lens which, for various reasons, fall short of being satisfactory. In U.S. Pat. No. 4,666,446 to Koziol et al., there is shown an intraocular lens having a complex shape for achieving a bi-focal result. The lens is held in place within the eye by haptics which are attached to the ciliary body. However, the implant requires the patient to wear spectacles for proper functioning. Another device shown in U.S. Pat. No. 4,944,082 to Richards et al., also utilizes a lens having regions of different focus, or a pair of compound lenses, which are held in place by haptics attached to the ciliary body. In this arrangement, contraction and relaxation of the ciliary muscle causes the haptics to move the lens or lenses, thereby altering the effective focal length. There are numerous other patented arrangements which utilize haptics connected to the ciliary body, or are otherwise coupled thereto, such as are shown in U.S. Pat. No. 4,932,966 to Christie et al., U.S. Pat. No. 4,888,012 to Home et al. and U.S. Pat. No. 4,892,543 to Turley, and rely upon the ciliary muscle to achieve the desired alteration in lens focus.

In any arrangement that is connected to the ciliary body, by haptic connection or otherwise, extensive erosion, scarring, and distortion of the ciliary body usually results. Such scarring and distortion leads to a disruption of the local architecture of the ciliary body and thus causes failure of the small forces to be transmitted to the intraocular lens. Thus, for a successful long-term implant, connection and fixation to the ciliary body is to be avoided if at all possible.

In U.S. Pat. No. 4,842,601 to Smith, there is shown an accommodating intraocular lens that is implanted into and floats within the capsular bag. The lens comprises front and rear flexible walls joined at their edges, which bear against the anterior and posterior inner surfaces of the capsular bag. Thus, when the zonules exert a tensional pull on the circumference of the capsular bag, the bag, and hence the intraocular lens, is flattened, thereby changing the effective power of refraction of the lens. The implantation procedure requires that the capsular bag be intact and undamaged and that the lens itself be dimensioned to remain in place within the bag without attachment thereto. Additionally, the lens must be assembled within the capsular bag and biasing means for imparting an initial shape to the lens must be activated within the capsular bag. Such an implantation is technically quite difficult and risks damaging the capsular bag, inasmuch as most of the operations involved take place with tools which invade the bag. In addition, the Smith arrangement relies upon pressure from the anterior and posterior walls of the capsular bag to deform the lens, which requires that the lens be extremely resilient and deformable. However, the more resilient and soft the lens elements, the more difficult assembly within the capsular bag becomes. Furthermore, fibrosis and stiffening of the capsular remnants following cataract surgery may make this approach problematic.

U.S. Pat. No. 6,197,059 to Cumming and U.S. Pat. No. 6,231,603 to Lang each disclose an intraocular lens design where the configuration of a hinged lens support ostensibly allows the intraocular lens to change axial position in response to accommodation and thus change effective optical power. U.S. Pat. No. 6,299,641 to Woods describes another intraocular lens that also increases effective focusing power as a result of a change in axial position during accommodation. In each of these intraocular lenses, a shift in axial position and an increase in distance from the retina results in a relative increase in focusing power. All lenses that depend upon a shift in the axial position of the lens to achieve some degree of accommodation are limited by the amount of excursion possible during accommodation.

U.S. Pat. No. 5,607,472 to Thompson describes a dual-lens design. Prior to implantation, the lens is stressed into a non-accommodative state with a gel forced into a circumferential expansion channel about the lens. At implantation, the surgeon must create a substantially perfectly round capsulorrhexis, and insert the lens therethrough. A ledge adjacent to the anterior flexible lens is then bonded 360° around (at the opening of the capsulorrhexis) by the surgeon to the anterior capsule to secure the lens in place. This approach has numerous drawbacks, a few of which follow. First, several aspects of the procedure are substantially difficult and not within the technical skill level of many eye surgeons. For example, creation of the desired round capsulorrhexis within the stated tolerance required is particularly difficult. Second, the bonding "ledge" may disrupt the optical image produced by the adjacent optic. Third, intraocular bonding requires a high degree of skill, and may fail if the capsulorrhexis is not 360° round. Fourth, the proposed method invites cautionary speculation as to the result should the glue fail to hold the lens in position in entirety or over a sectional region. Fifth, it is well known that after lens implantation surgery the capsular bag, upon healing, shrinks. Such shrinking can distort a lens glued to the bag in a pre-shrunk state, especially since the lens is permanently affixed to a structure which is not yet in equilibrium. Sixth, Thompson fails to provide a teaching as to how or when to release the gel from the expansion channel; i.e., remove the stress from the lens. If the gel is not removed, the lens will not accommodate. If the gel is removed during the procedure, the lens is only in a flattened non-accommodating shape during adhesion to the capsule, but not post-operatively, and it is believed that the lens therefore will fail to interact with the ciliary body as required to provide the desired accommodation as the capsular bag may change shape in the post-operative period. If the gel is otherwise removed thereafter, Thompson ostensibly requires an additional surgical procedure therefor. In view of these problems, it is doubtful that the lens system disclosed by Thompson can be successfully employed.

Thus, the prior art discloses numerous concepts for accommodating intraocular lenses. However, none are capable of providing an accommodating implant which does not, in one way or another, risk damage to the ciliary body or the capsular bag, present technical barriers, or present potential serious consequences upon failure of the device.

SUMMARY OF THE INVENTION

It is therefore an object of the invention to provide an intraocular lens that functions similarly to the natural crystalline lens.

It is another object of the invention to provide an intraocular lens that changes shape and increases power during accommodation.

It is also an object of the invention to provide an intraocular lens that produces a sufficient increase in focusing power such that it is clinically useful.

It is an additional object of the invention to provide an intraocular lens that permits uncomplicated implantation of the lens in a manner compatible with modern-day cataract surgery techniques.

In accord with these objects, which will be discussed in detail below, an intraocular lens (IOL) system that permits accommodation and a method of implanting such an intraocular lens system are provided. Generally, the invention includes an intraocular lens that is maintained in a stressed non-accommodating configuration during implantation into the capsular bag of the eye and maintained in the stressed configuration during a post-operative healing period during which the capsular bag heals about the lens. After the post-operative healing period, the intraocular lens is preferably atraumatically released from the stressed state and permitted to move between accommodative and non-accommodative configurations in accord with stresses placed thereon by the ciliary body and other physiological forces.

According to one embodiment of the invention, the intraocular lens system includes a flexible optic having a skirt (periphery or haptic), and a restraining element about the skirt and adapted to temporarily maintain the flexible optic in a stressed, non-accommodating configuration during a post-operative period. The retraining element may comprise a dissolvable bioabsorbable material such that the element automatically releases the optic after a post-operative period, or may be released under the control of a eye surgeon, preferably via a non-surgically invasive means such as via a laser or a chemical agent added to the eye.

According to another embodiment of the invention, the intraocular lens system includes an optic, a pair of haptics located on sides of the optic, and hinge portions at each of the optic haptic junctions. The hinge portions have stressed and non-stressed state configurations. In accord with the invention, one or more restraining elements are provided to maintain the stressed state configuration of the hinge portion during implantation and during a post-operative period.

Generally, the method includes (a) inducing cycloplegia; (b) providing an intraocular lens having an optic portion and haptics and having an as manufactured bias induced between the optic portion and haptics, the intraocular lens being held in a non-accommodating stressed state by a restraining means such that the intraocular lens has a lower optical power relative to an accommodating non-stressed state of the lens; (c) inserting the stressed state intraocular lens into a capsular bag of the eye; (d) maintaining cycloplegia until the capsular bag physiologically affixes to the intraocular lens; and (e) non-surgically invasively releasing the restraining means to permit the intraocular lens to move from the stressed state into the non-stressed state in which the intraocular lens has an increased optical power, and wherein the optical power of the intraocular lens is reversibly adjustable in response to stresses induced by the eye such that the lens can accommodate.

More particularly, according to a preferred method of implantation, the ciliary body muscle is pharmacologically induced into a relaxed stated (cycloplegia), a capsulorrhexis is performed on the lens capsule, and the natural lens is removed from the capsule. The prosthetic lens is then placed within the lens capsule. According to a preferred aspect of the invention, the ciliary body is maintained in the relaxed state for the duration of the time required for the capsule to naturally heal and shrink about the lens; i.e., possibly for several weeks. After healing has occurred, the restraining element automatically or under surgeon control releases the lens from the stressed state. The ciliary body and lens may then interact in a manner substantially similar to the physiological interaction between the ciliary body and a healthy natural crystalline lens.

Alternatively, a fully relaxed lens (i.e., without restraining element) can be coupled to a fully stressed and contracted ciliary body.

The intraocular lens system of the invention is compatible with modern cataract surgery techniques and allows for large increases in optical power of the implanted lens. Unlike other proposed accommodating intraocular lens systems, the lens described herein is capable of higher levels of accommodation and better mimics the function of the lens of the human eye. Further, unlike other lens systems previously described, the lens take into account certain reciprocal aspects of the relationship between the natural crystalline lens and the ciliary body. Moreover, the implantation is relatively easy and rapid.

Additional objects and advantages of the invention will become apparent to those skilled in the art upon reference to the detailed description taken in conjunction with the provided figures.

BRIEF DESCRIPTION OF THE DRAWINGS

FIG. 9 is a transparent front view of an intraocular lens according to the invention shown with a second embodiment of a restraining element;

FIG. 10 is a schematic transverse view of the intraocular lens of FIG. 9;

FIG. 15 is a schematic front view of an intraocular lens according to the invention having a particular skirt configuration which include haptics and another alternate embodiment restraining element;

FIG. 16 is a schematic front view of another intraocular lens according to the invention having a particular skirt configuration which include haptics and yet another alternate embodiment restraining element;

FIG. 17 is a schematic side view of the intraocular lens of FIG. 16;

FIG. 18 is an intraocular lens according to the invention having a particular skirt configuration which include haptics and yet a further alternate embodiment restraining element;

FIG. 22 is a schematic front view of a second embodiment of an intraocular lens according to the invention, shown in a stressed configuration;

FIG. 23 is a schematic side view of the intraocular lens of FIG. 22, shown in a stressed configuration;

FIG. 24 is a schematic side view of the intraocular lens of FIG. 22, shown in a non-stressed configuration;

FIG. 27 is a schematic front view of an intraocular lens according to the invention having four haptics;

DETAILED DESCRIPTION OF THE PREFERRED EMBODIMENTS

Figure 3:
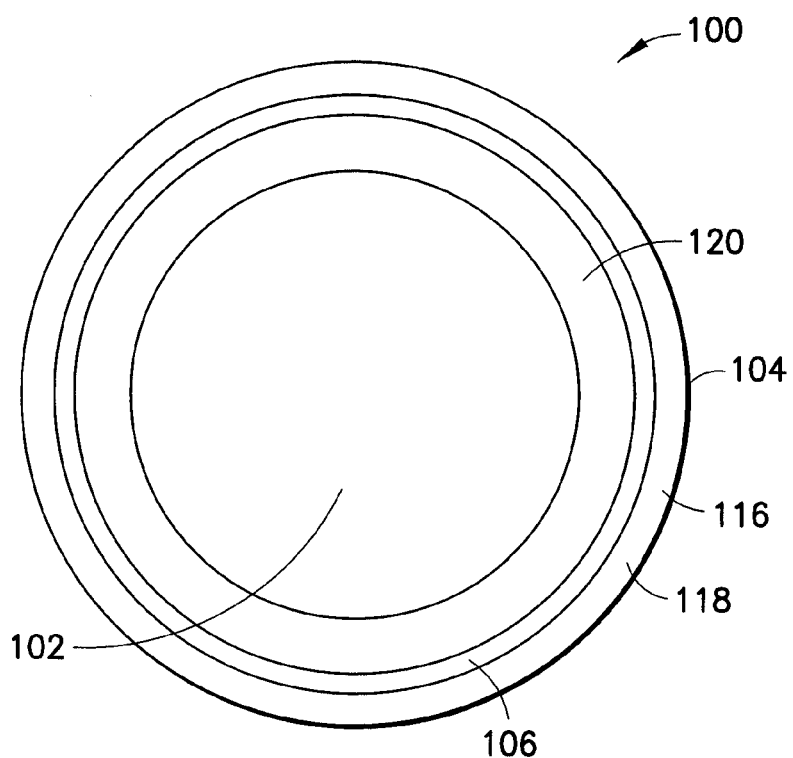
FIG. 3 is a schematic front view of an intraocular lens according to the invention configured into a stressed state with a restraining element.
Figure 8:
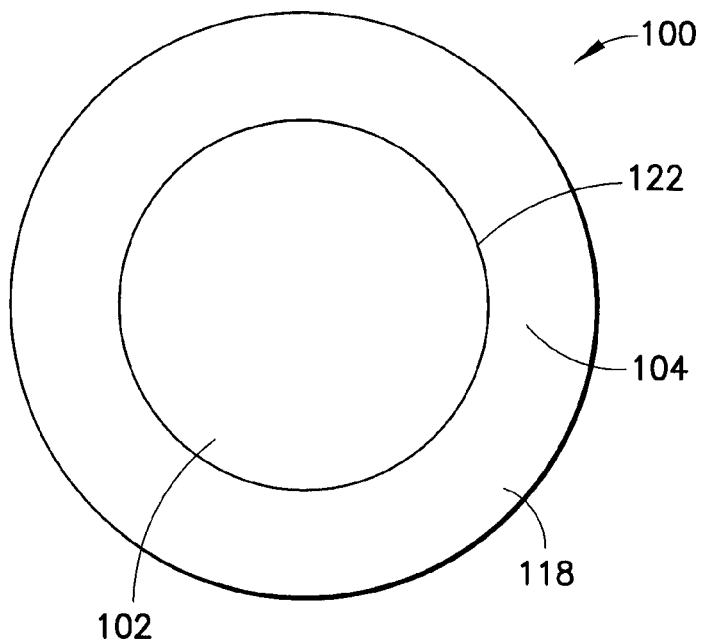
FIG. 8 is a schematic front view of an intraocular lens according to the invention with the restraining element removed, and thus, configured in a non-stressed accommodating state.

Turning now to FIG. 3, a first preferred embodiment of an intraocular lens 100 according to the invention is shown. The lens includes a pliable optic portion 102 having an elastic memory, and is peripherally surrounded by a skirt portion 104. A restraining element 106 is provided on the skirt portion 104 and operates to hold the skirt portion and optic portion 102 in a stressed (i.e., stretched) configuration. Comparing FIG. 3, showing the optic portion in a stressed configuration, with FIG. 8, showing the optic portion in a non-stressed configuration, it is seen that the optic portion has a smaller diameter in the non-stressed configuration.

Figure 4:
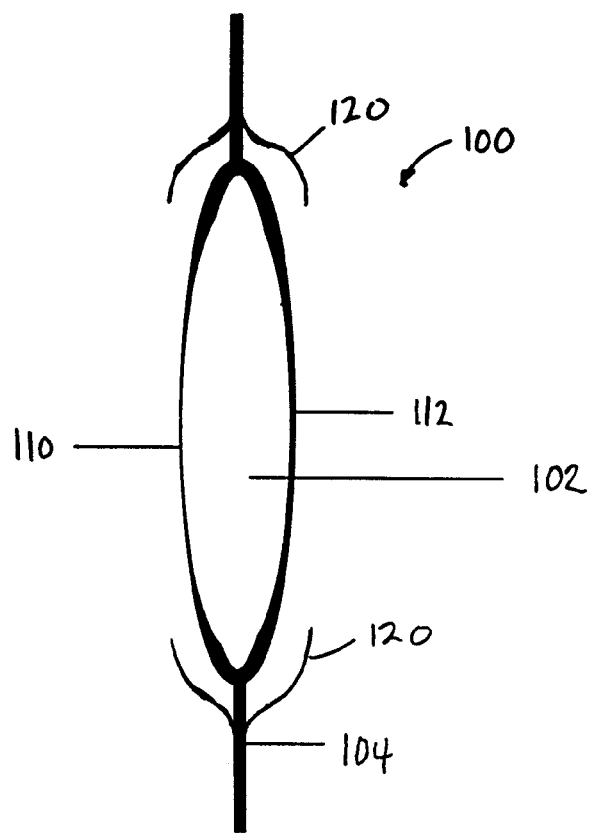
FIG. 4 is a schematic transverse section view of the intraocular lens of FIG. 3 in a stressed state.
Figure 5:
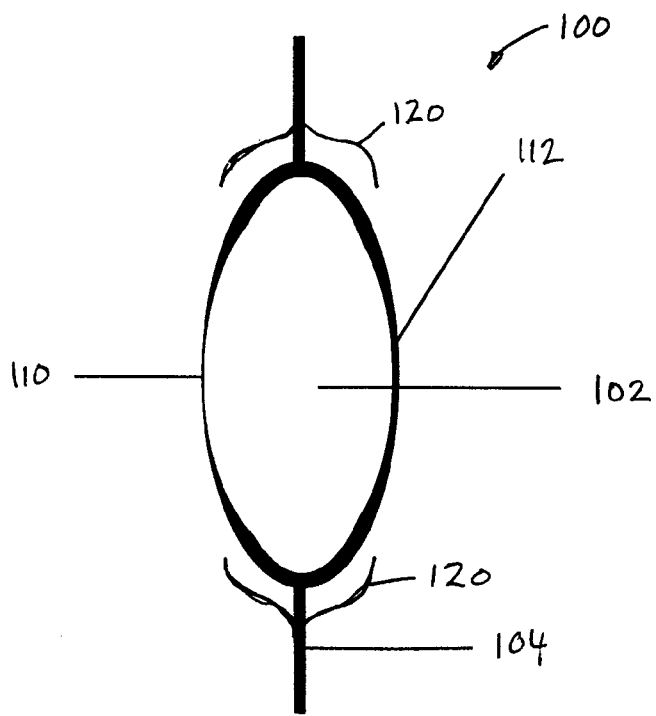
FIG. 5 is a schematic transverse section view of the intraocular lens of FIG. 3 in a non-stressed accommodating state.
Figure 7:
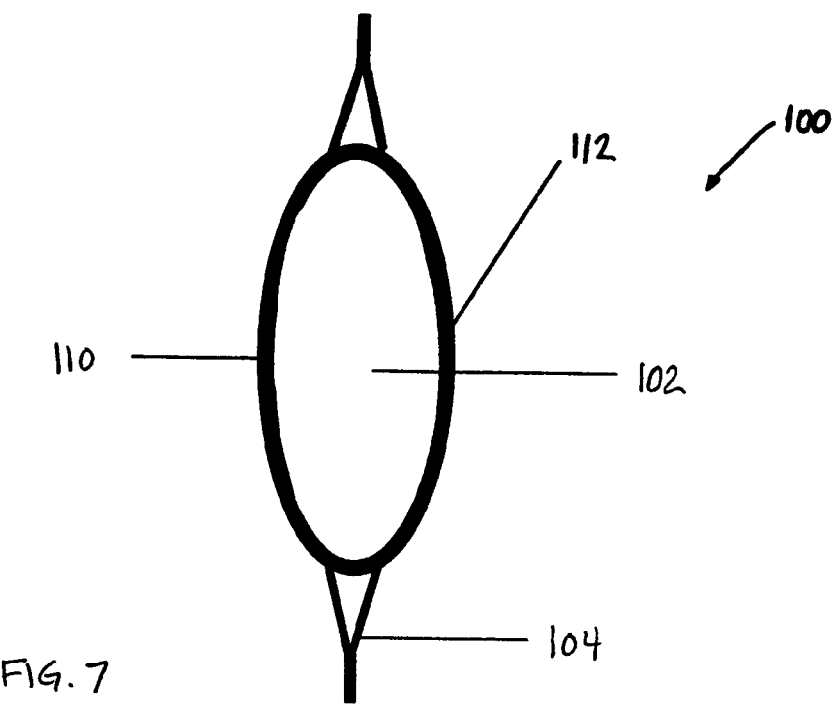
FIGS. 6 and 7 are other schematic transverse section views of intraocular lenses according to the invention.
Figure 6:
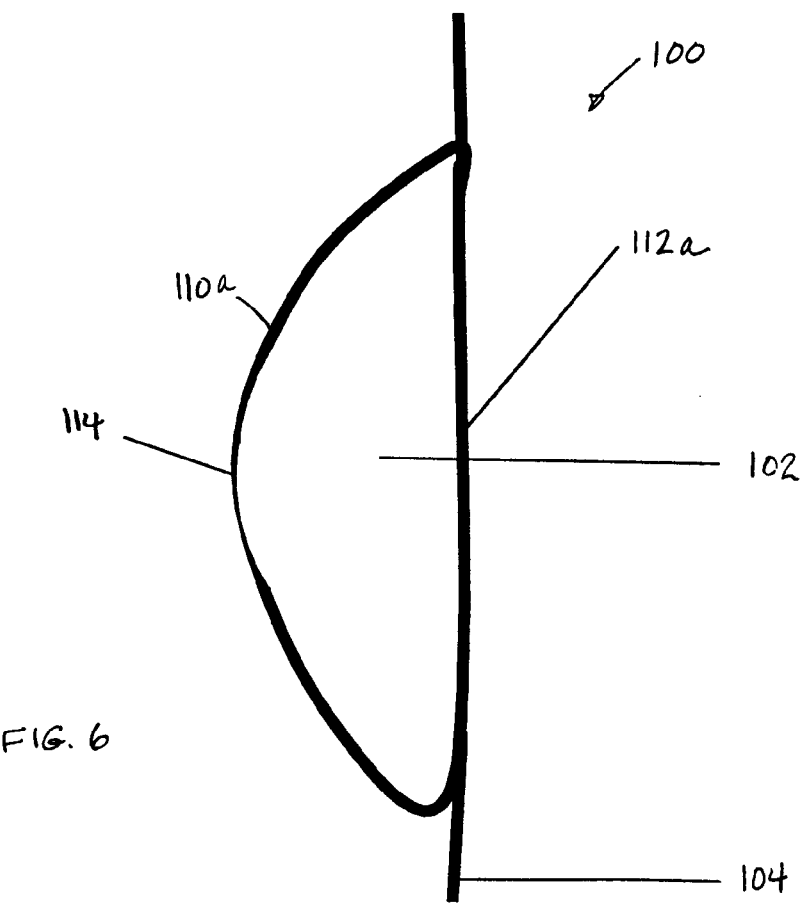

More particularly, the optic portion 102 is typically approximately 5 to 6 mm in diameter and made from a silicone polymer or other suitable flexible polymer. The optic portion defines an anterior surface 110 and a posterior surface 112. The optic portion may have a biconvex shape in which each of the anterior surface 110 and posterior surface 112 have similar rounded shapes. FIG. 4 illustrates such a lens in a stressed non-accommodating configuration, while FIG. 5 illustrates such a lens in the non-stressed accommodating configuration. Alternatively, referring to FIG. 6, the anterior surface 110a may be provided with a substantially greater curvature than the posterior surface 112a. In addition, referring to FIG. 7, the anterior and posterior surfaces 110, 112 of the optic portion can be evenly pliable throughout, or, referring back to FIG. 6, greater flexibility and pliability can be fashioned into the central portion 114 of the anterior 110 surface of the lens to enhance the accommodating effect. This may be done by using materials of differing modulus of elasticity or by altering the thickness of the central portion and/or anterior surface 110 of the optic portion 102.

Referring back to FIG. 3, the skirt portion 104 has substantially less pliability than the optic portion 102. The periphery 116 of the skirt portion 104 is preferably provided with a plurality of circumferentially displaced fenestration holes 118. The fenestration holes 118 operate to promote firm attachment of the capsular bag to the lens skirt 104 during the healing period. That is, during the healing process, the capsular bag shrinks by a substantial amount and portions of the anterior and posterior capsular bag enter into the fenestration holes 118 and join together to lock the lens 100 within the capsule without necessitating any bonding agent, sutures, or the like. Alternatively, the peripheral portion 104 could be fashioned with a textured surface, ridges or any surface modification that promotes strong adhesion of the capsule to the lens skirt 104.

Referring to FIGS. 3 and 4, according to a preferred, though not essential, aspect of the invention, a preferably thin and pliable collar 120 is positioned around the anterior surface of lens near the junction 122 (FIG. 8) of the optic portion 102 and the skirt portion 104 to keep the more central portions of the anterior capsular remnant from adhering to the optic portion. The collar is preferably made from silicone or another smooth polymer.

As discussed above, the skirt portion 104 is maintained in a stressed configuration by the restraining element until the restraining element is removed. According to a preferred embodiment of the restraining element, the restraining element is a band provided on the outside of the skirt portion. The band 106 is preferably comprised of a dissolvable, preferably bioabsorbable material that is adapted to preferably naturally dissolve in the fluid of the eye within a predetermined period of time after implantation. Alternatively, the dissolvable material may be selected so that it dissolves only upon the addition of a dissolving-promoting agent into the eye. Preferred dissolvable materials for the restraining band 106 include collagen, natural gut materials, glycan, polyglactin, poliglecaprone, polydioxanone, or other carbohydrate-based or protein-based absorbable material.

Referring now to FIGS. 9 and 10, according to a second embodiment of the restraining element 106a, the restraining element comprises a circumferential channel 130a in the skirt 104 that is filled with a fluid or gel 132a. Preferably an isotonic solution such as a balanced salt solution is used. Alternatively, other suitable fluids, solution, or gels, including viscoelastics can be used. The channel 130a has an outlet 134a that is blocked by a dissolvable, preferably bioabsorbable seal 136a. The filled channel 130a operates to stress the optic portion 102 into a non-accommodating configuration until the seal 136a is dissolved and the outlet 134a is thereby opened. Then, the material 132a within the channel 130a is forced out of the channel by the natural elasticity of the lens and permits the lens to move in accord with the excitation state of the ciliary body; i.e., between non-accommodative and accommodative states. Alternatively, the seal material 136a may not be naturally dissolvable within the environment of the eye, but rather is dissolvable within the presence of a chemical agent, such as an enzyme, which can be added to the eye. In such case, the eye surgeon can non-surgically control the release of the seal.

Figure 11:
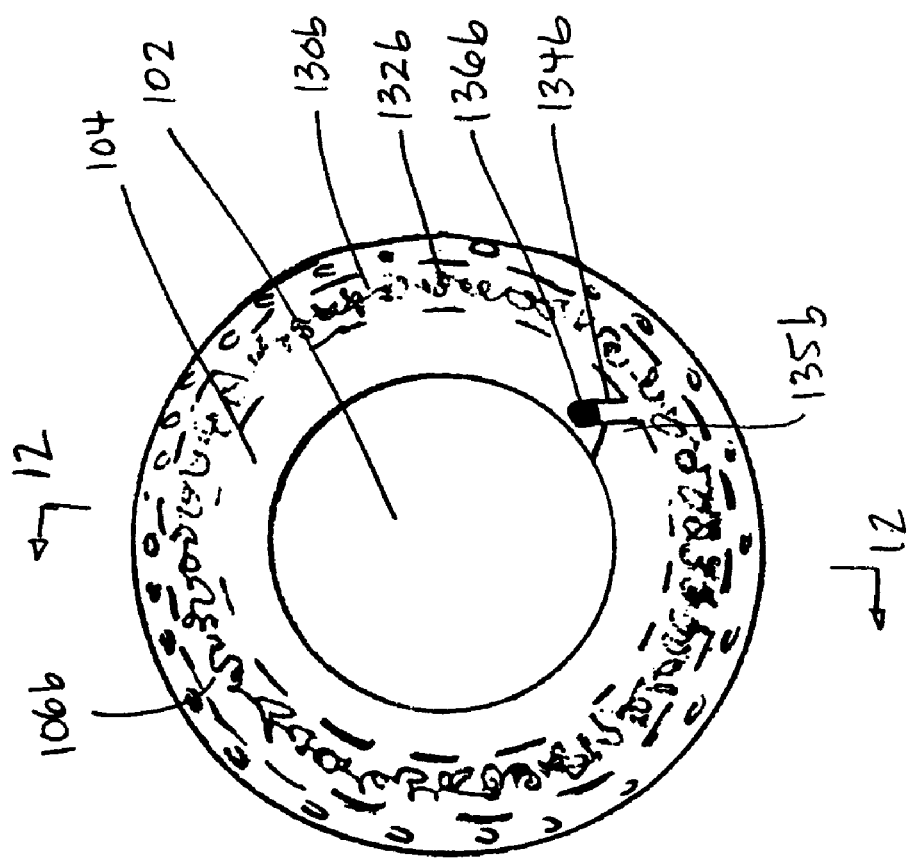
FIG. 11 is a transparent front view of an intraocular lens according to the invention shown with a third embodiment of a restraining element.
Figure 12:
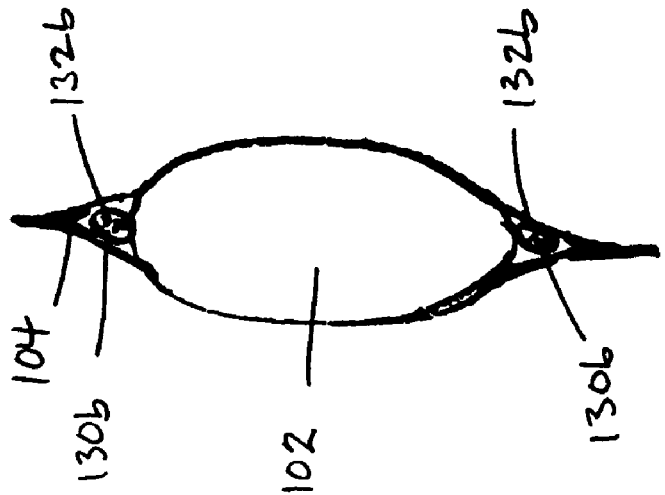
FIG. 12 is a schematic transverse view of the intraocular lens of FIG. 11.

Turning now to FIGS. 11 and 12, according to a third embodiment of the restraining element, the restraining element 106b comprises a circumferential channel 130b in the skirt portion 104 that is filled with a balanced salt solution or other suitable material 132b that maintains the optic portion into a non-accommodating stressed configuration. The channel 130b has an outlet tube 134b that is biased outward from the optic portion 108 but which is preferably anchored with an anchor 135b toward the optic portion 102 but which preferably does not overlie a central area of the optic portion which would interrupt the vision of the patient when the lens is implanted. The outlet tube 134b is provided with a seal 136b made from a material, e.g., hard silicone, polymethylmethacrylate (PMMA) or plastic, that is ablatable or otherwise able to be unsealed by laser light from a YAG laser or other laser suitable for eye surgery. Likewise, the anchor 135b is also made from such a material. When the lens is implanted, as discussed in detail below, the anchor 135b and the outlet tube 134b, by being directed toward the optic portion 102, is visible to the eye surgeon through a dilated iris and is positioned to receive laser light. In this embodiment, the seal 136b can be removed and the outlet tube 134b opened under the full control of the eye surgeon (at his or her discretion upon post-operative evaluation of the lens recipient) by use of a laser to remove the pressure in the channel 130b to equilibrate with the anterior chamber pressure of the eye. Moreover, removal of the anchor 135b enables the outlet tube to move away from the optic portion in accord with its bias and toward the periphery to minimize any potential interference with the patient's vision.

Figure 14:
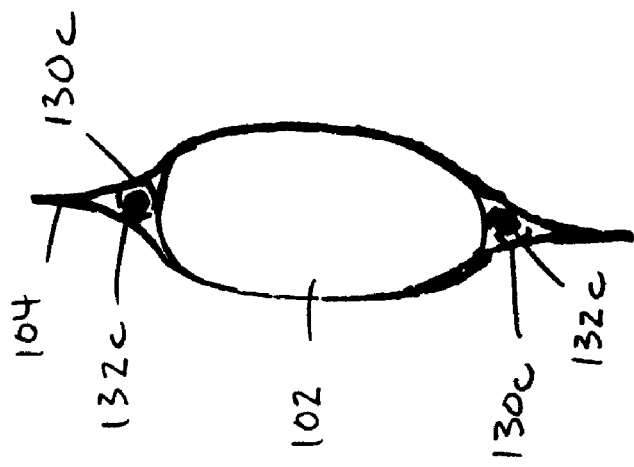
FIG. 14 is a schematic transverse view of the intraocular lens of FIG. 13.
Figure 13:
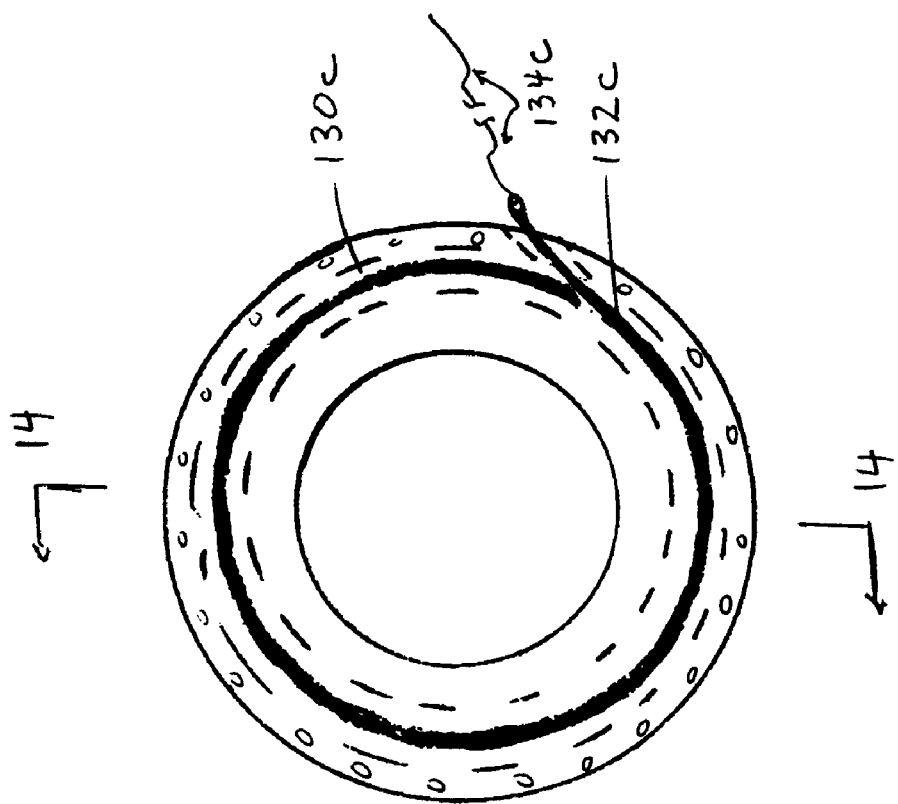
FIG. 13 is a transparent front view of an intraocular lens according to the invention shown with a fourth embodiment of a restraining element.

According to a fourth embodiment of the restraining element, any mechanical means for maintaining the lens in a stressed configuration can be used. For example, referring to FIGS. 13 and 14, a relatively stiff restraining element 132c having a circular form can be inserted or otherwise provided within a circumferential channel 130c. The restraining element is made from a material designed to be ablated or broken upon receiving laser energy, e.g., hard silicone, polymethylmethacrylate (PMMA) or plastic. Alternatively, the end of the element 132c can be provided with a length of flexible material 134c, e.g., suture, which can be extended to outside the eye. When it is desired to remove the restraining element, the surgeon grasps the suture with a forceps and pulls the suture. This either removes the restraining element from the lens or breaks the restraining element. In either case, the stress is released from the optic. As yet another less preferred alternative, stiff restraining element is removable or broken only upon an invasive (requiring an incision) surgical procedure.

Other embodiments for the restraining elements and removal thereof are possible. For example, and not by way of limitation, the seal for an inflated channel can be attached to a suture or other length of flexible material which extends outside the eye. The suture can be pulled by the surgeon to remove the seal. In yet another example, shallow shells, adapted to be dissolvable naturally or in conjunction with an additive agent, may be provided to the front and back of the optic portion to force the optic portion to adopt a flatter (i.e., stressed) configuration. By way of another example, dissolvable or laser-removable arced struts may be provided across the lens which force the optic portion into a stressed state.

Moreover, embodiments of the restraining element which maintain the stressed state of the optic via external flattening of the optic or by arced struts are suitable for use with a non-circumferential skirt portion; i.e., where the skirt portion is defined by a plurality of haptics extending outward from the optic portion. For example, FIGS. 15-18, illustrate the "skirt portion" defined by a plurality of haptics, rather than a complete ring about the optic. FIG. 15 discloses a skirt portion 104a defined by three haptics 140a, each of which preferably includes fenestration holes 118a. Dissolvable or laser-ablatable arced struts 142a are situated to maintain a radial stress on the optic portion 102a; i.e., the struts 142a function together as a restraining member. FIGS. 16 and 17 discloses a skirt defined by four haptics 140b, each of which preferably includes fenestration holes 118b. Shells 144b are coupled to the haptics anterior and posterior of the optic to flatten the optic. FIG. 18 discloses a skirt defined by two haptics 140c, each of which preferably includes fenestration holes 118*c*. Multiple struts 142*c* are coupled to each haptic 140*c*.

In addition, it is recognized that the optic portion may be provided in an optically transparent bag, and the bag may be pulled or otherwise forced taught to stress the optic. The bag may be pulled taught by using one of the restraining element described above, e.g., retaining rings, channels, shells, or struts, or any other suitable means, provided either directly to the bag or provided to an element coupled about a periphery of the bag.

Moreover, it is recognized that the lens of the invention may comprise two optic elements: one stationary and the other adapted to change shape and thereby alter the optic power of the dual optic system. In such an embodiment, the optic element adapted to change shape would be provided in a stressed-configuration, according to any embodiment described above.

In each embodiment of the restraining element, the restraining element is preferably configured on or in the lens during manufacture, such that the lens is manufactured, shipped, and ready for implant in a fully stressed configuration.

Figure 19:
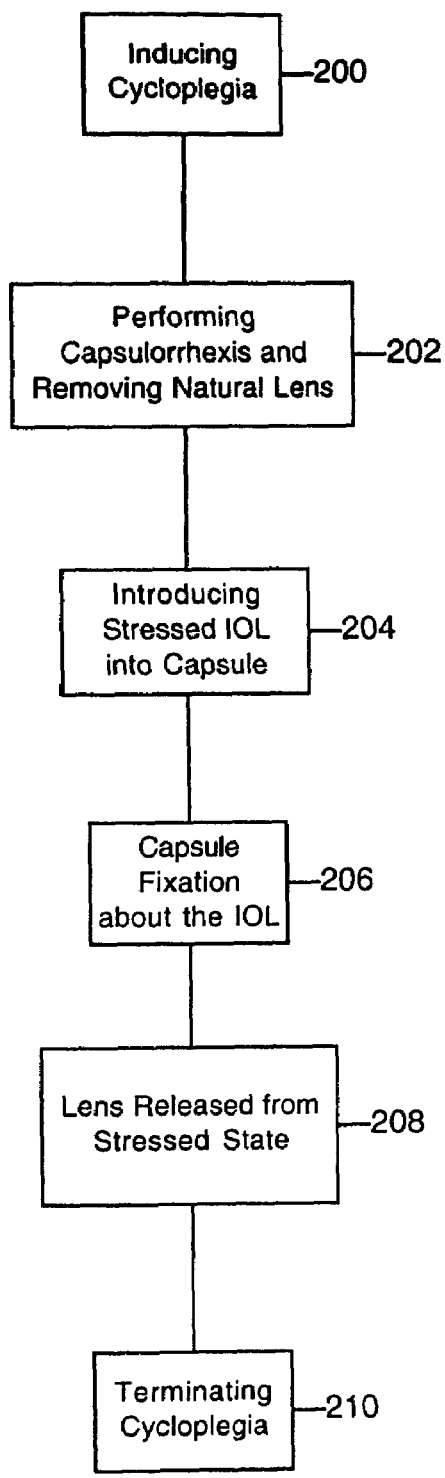
FIG. 19 is a block diagram of a first embodiment of a method of implanting an intraocular lens according to the invention.

The lens is implanted according to a first method of implantation, as follows. Referring to FIG. 19, the patient is prepared for cataract surgery in the usual way, including full cycloplegia (paralysis of the ciliary body) at 200. Cycloplegia is preferably pharmacologically induced, e.g., through the use of short-acting anticholinergics such as tropicamide or longer-lasting anticholinergics such as atropine.

An anterior capsulorrhexis is then performed at 202 and the lens material removed. A stressed lens according to the invention is selected that preferably has an optic portion that in a stressed-state has a lens power selected to leave the patient approximately emmetropic after surgery. The lens is inserted into the empty capsular bag at 204.

Cycloplegia is maintained for several weeks (preferably two to four weeks) or long enough to allow the capsular bag to heal and "shrink-wrap" around the stressed and elongated lens at 206. This can be accomplished post-operatively through the use of one percent atropine drops twice daily. As the lens shrinks, the anterior and posterior capsular bag walls enter into the fenestration holes and join together to lock the lens in position.

If the lens includes a restraining element having a dissolvable component, eventually the dissolvable material is lost from the lens, and the lens is unrestrained. If the lens includes a restraining element having a laser-removable component, a surgeon may at a desired time remove the component to place the lens in a unrestrained configuration. If the lens includes a retraining element which must be surgical removed or altered, the surgeon may at a desired time perform a second eye procedure to remove the component and place the lens in an unrestrained configuration.

Figure 1:
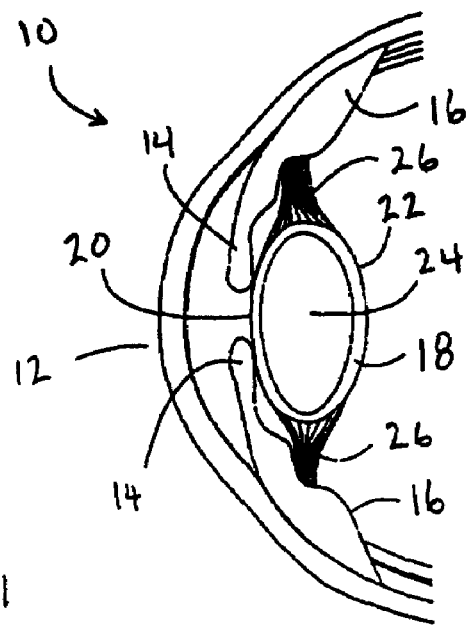
FIG. 1 is a diagrammatic view of a cross-section of a normal eye.
Figure 2:
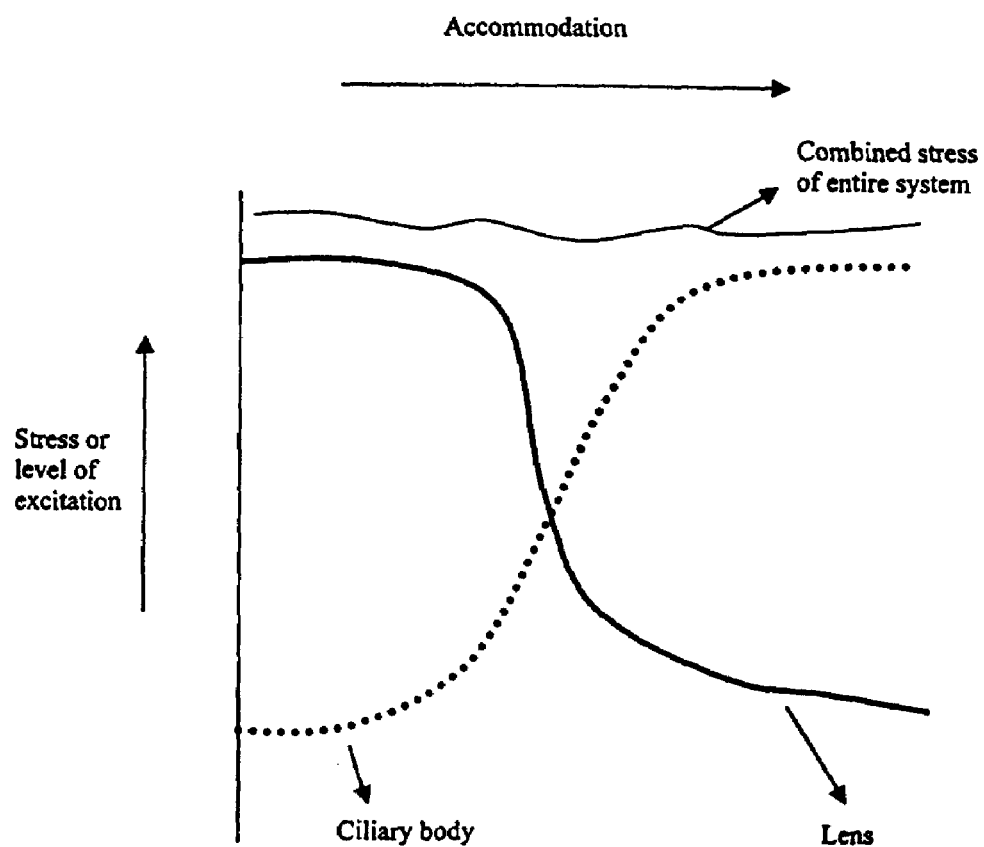
FIG. 2 is a graph of the stresses on the ciliary body-crystalline lens system of the eye in a continuum of states between distance vision and full accommodation.

Regardless of the method used, when the lens is unrestrained (i.e., released from the stressed state) at 208 and the post-operative cycloplegic medicines are stopped at 210 the lens is initially still maintained in a stressed state (FIG. 4) due to the inherent zonular stress of the non-accommodating eye. When the patient begins accommodating, the zonular stress is reduced and the implanted lens is permitted to reach a more relaxed globular conformation, as shown in FIGS. 5 and 8. This change in shape provides the optic with more focusing power and thus accommodation for the patient is enabled. As with the natural crystalline lens, the relaxation of the implanted lens to a more globular shape is coupled with a development of strain or stress in the ciliary body during accommodation. Further, when the patient relaxes accommodation, the stress in the ciliary body is reduced, and there is a compensatory gain in stress as the lens is stretched into its non-accommodative shape (See again FIG. 2).

Figure 20:
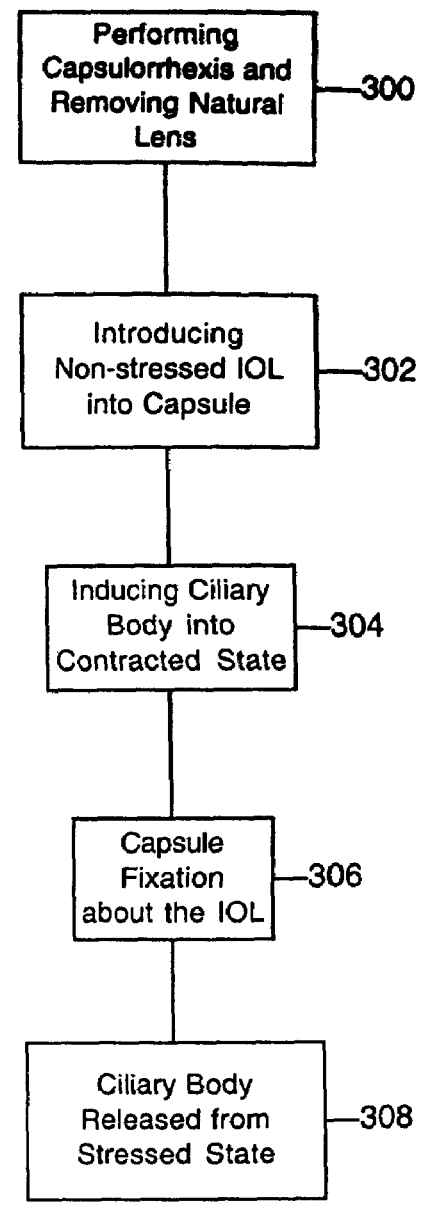
FIG. 20 is a block diagram of a second embodiment of a method of implanting an intraocular lens according to the invention.

Referring to FIG. 20, according to another embodiment of the method of the invention, a lens of similar design as described above is used, except that there is no restraining element on the lens. Temporary cycloplegia is induced, and a capsulorrhexis is performed 300. The lens is implanted while the ciliary body is in a fully relaxed state at 302. The patient is then fully accommodated (i.e., the ciliary body is placed in a contracted state) at 304, preferably through pharmacological agents such as pilocarpine.

Once the capsular bag is fully annealed (affixed) to the lens periphery at 306, the pharmacological agent promoting accommodation is stopped at 308. Then, as the ciliary body relaxes, the lens is stretched into an elongated shape having less focusing power. Conversely, as accommodation recurs, the lens returns to it resting shape having greater focusing power.

Figure 21:
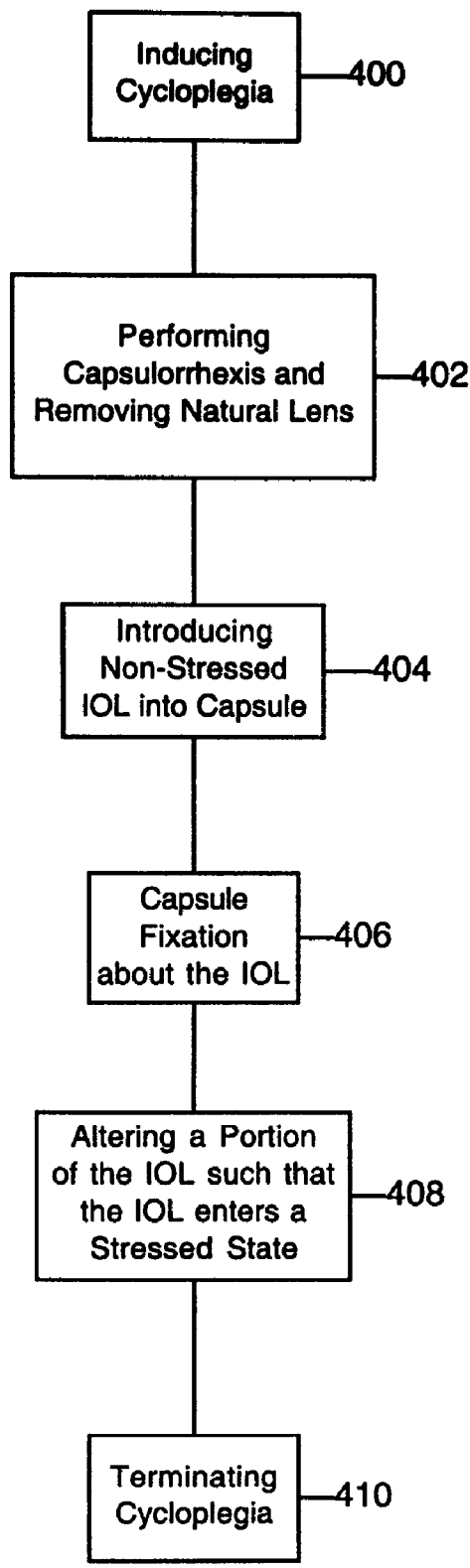
FIG. 21 is a block diagram of a third embodiment of a method of implanting an intraocular lens according to the invention.

Referring to FIG. 21, in yet another embodiment of the method of the invention, the patient is cycloplegged during cataract surgery at 400, a capsulorrhexis is performed at 402, and a flexible lens in an unstressed state is implanted in the capsular bag at 404. After a few weeks of complete cycloplegia and during which capsular fixation of the lens periphery is accomplished at 406, light (e.g., ultraviolet or infrared), a chemical agent, or another suitable means is used to shrink or otherwise alter the optic or the adjacent skirt of the lens while the patient is still fully cycloplegged at 408. In this manner, the optic is again placed into a stressed configuration while the ciliary body is fully relaxed. As with previous embodiments, when cycloplegia is stopped and accommodation occurs at 410, the lens is able to return to a more relaxed globular configuration.

The intraocular lens systems described with respect to FIGS. 1 through 18 operate to provide accommodation through a change in shape in the optic resulting from an equilibrium of the anatomical forces and the forces in the lens. As now described, it is also possible to provide accommodation through axial movement of a lens within the eye, all while maintaining equilibrium between the anatomical forces and the structural stress designed into the lens.

Figure 25:
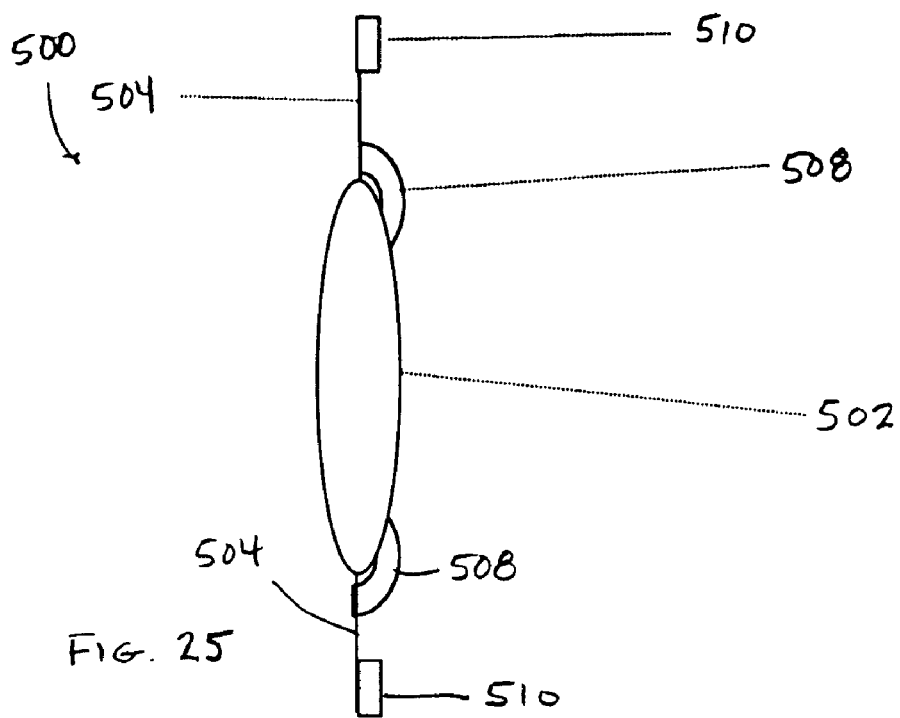
FIG. 25 is a schematic side view of the intraocular lens according to the second embodiment of the invention held in a stressed configuration with a bridge-type restraining element.
Figure 26:
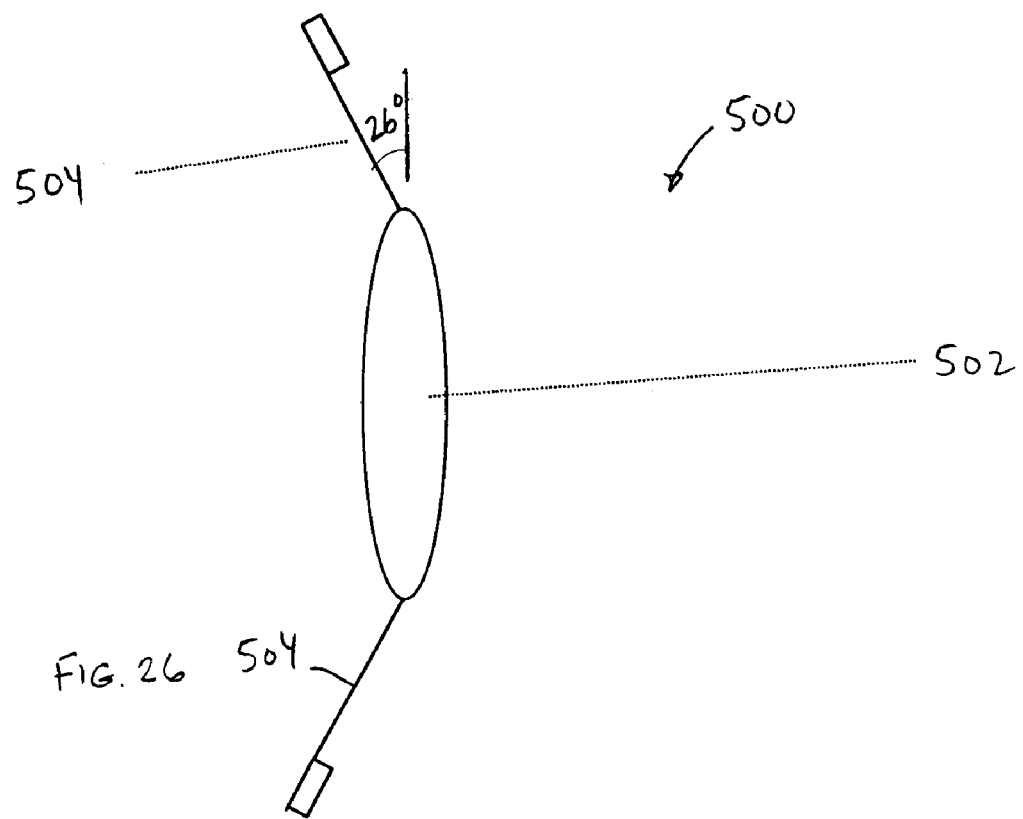
FIG. 26 is a schematic side view of the intraocular lens of FIG. 25 shown in a non-stressed configuration.

Turning now to FIG. 22 through 24, an embodiment of another intraocular lens system according to the invention is shown. The lens 500 includes a central optic 502, two peripheral haptics 504, and a junction 506 between the optic 502 and the haptics 504. The junction 506 preferably has an elastic memory such that, in a relaxed configuration of the lens 500, free ends 505 of the haptics 504 are oriented at a posterior angle a relative to the optic 502 (FIG. 24); i.e., there is a bias induced between the optic and haptics along an anterior-posterior axis A. A preferred range for angle a includes 1 to 60 degrees, with a more preferred angle a being 25 to 35 degrees. The junction 506 can be a skirt portion attached about the periphery of the optic, or can be integrated into the periphery of the optic, particularly where the optic and junction are unitarily formed as one piece from a flexible polymeric material. In addition, the junction 506 can vary in size allowing elastic bias over part or all of the haptic. For instance, the unstressed conformation of the haptic can describe an arc over all or part of its length. A restraining element 508 is preferably provided either at the junction 506 to restrain flexing at the junction (FIGS. 22) or extends as a bridge from the optic 502 to the haptics 504 (FIG. 25) to maintain the lens 500 in a stressed preferably substantially planar configuration during implantation and for a post-operative period. Alternatively, the stressed configuration can be any configuration of the lens in which the optic is oriented in a more posterior orientation relative to the haptic than in the non-stressed configuration. When the restraining element 508 is removed, the haptics 504 are biased toward an angled configuration relative to the optic 502, with the optic moved anteriorly relative to the haptics (FIG. 26). In accord with the above, when the lens 500 is restrained in the stressed configuration, the lens 500 has a total diameter (maximum peripheral extension from the peripheralmost end of one haptic 504 to the peripheralmost end of another haptic)(FIG. 23) that is larger than the total diameter of the lens when the lens is in the unrestrained unstressed configuration in which the haptics 504 bend relative to the optic 502 in accord with the bias induced along the anterior-posterior axis A (FIG. 24).

More particularly, the optic 502 can be a flexible construction, as in the previous embodiments, or may be substantially rigid. The optic is preferably fixed in power, but may contain zones of different optic power. As such, the optic is either constructed of a suitable flexible polymer such as a silicone polymer, or a suitable stiff plastic such as polymethylmethacrylate (PMMA). The optic preferably has a diameter of approximately 4 mm to 7 mm, and most preferably approximately 5 mm.

The haptics 504 can be substantially planar, curved or loop-like in structure; i.e., they may generally conform to any well-known haptic structure. Moreover, as shown in FIG. 27, there may be more than two haptics, e.g., four haptics 504a. Furthermore, as described with respect to the previous embodiments, the haptics 504 may be provided with any number of surface modifications, including knobs, protuberances, textures, fenestration holes, ridge, etc., that promote strong adhesion with the shrink-wrapped capsular remnant. For example, referring back to FIGS. 25 and 26, a peripheral ridge 510 may be provided to the haptics 504. The ridge 510 promotes adhesion as well as forces the lens into a more posterior portion of the capsular bag upon implantation, which may be desirable. In addition, the haptics may contain portions of varying flexibility, such as a more flexible peripheral extent to promote flexion of the peripheral haptic against the capsular rim.

The restraining elements 508, as described with respect to the earlier embodiments, are preferably bio-resorbable, chemically resorbable, laser-removable, or surgically removable. Any restraining element that is removable in the one of the above listed manners or in any other relatively atraumatic manner and which provides the necessary function of maintaining the lens in a relatively planar stressed configuration during implantation and during a post-operative period can be similarly used.

Figure 28:
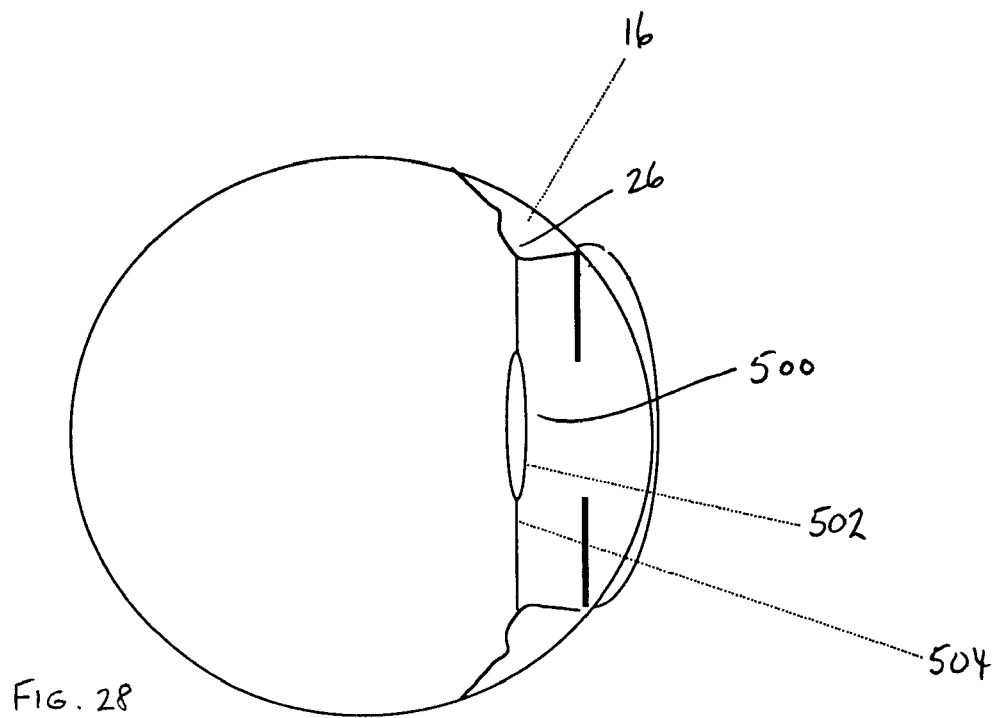
FIG. 28 is a diagrammatic view of a cross-section of an eye having an intraocular lens according to the second embodiment of the invention implanted therein, the lens being in a stressed configuration.

The lens 500 is implanted as described above. That is, cycloplegia is induced, an anterior capsulorrhexis is performed and the lens material removed. Referring to FIG. 28, the lens, in a stressed, substantially planar configuration is inserted into the empty capsular bag. Cycloplegia is maintained long enough to allow the capsular bag to heal, "shrink-wrap", and fibrose around the stressed lens. After the bag has healed, cycloplegia is terminated and the restraining element (not shown in FIG. 28) is removed.

Figure 29:
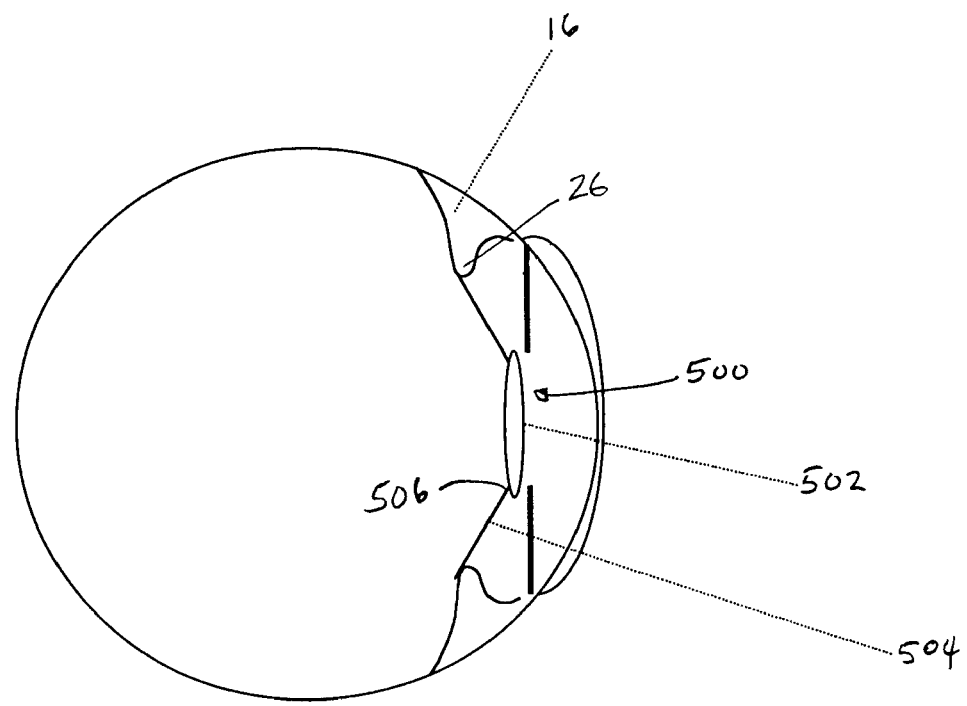
FIG. 29 is a diagrammatic view of a cross-section of an eye having an intraocular lens according to the second embodiment of the invention implanted therein, the lens being in a non-stressed configuration.

Referring to FIG. 29, with the lens unrestrained, the optic 502 of the lens 500 is able to move anteriorly forward during accommodation and increase the focusing power of the eye. The optic 502 moves forward for at least two reasons. First, with accommodation, the stress in the ciliary body 16 is increased causing constriction of the ciliary body, and resultant reduced tension on the zonules 26. This allows bending of the haptic-optic junction 506 back to its relaxed non-planar configuration. Second, during accommodation there is anterior movement of the ciliary body 16.

Then, when the patient relaxes accommodation, the stress in the ciliary body 16 is reduced and the ciliary body dilates and moves posteriorly. There is a compensatory gain in stress across the optic-haptic junction 506 as the junction is bent against its memory into a more planar configuration and the optic 502 moves posteriorly (See again FIG. 28).

In addition, as discussed above with respect to the first embodiment, a photoreactive intraocular lens may be implanted in an unstressed state. After capsular fixation of the lens, light (e.g., ultraviolet or infrared), a chemical agent, or another suitable means is used to alter the optic into a stressed configuration while the ciliary body is fully relaxed. Then, when cycloplegia is stopped and accommodation occurs, the lens is able to return to non-stressed configuration in which the lens is located anteriorly relative to the haptic portion.

Moreover, as also discussed above with respect to the first embodiment, the lens can be implanted in the eye in a non-stressed configuration, and the ciliary can be pharmacologically induced to contract during the healing period. After healing, pharmacological inducement of ciliary contraction is stopped, and the lens operates in the same manner as described above.

There have been described and illustrated herein several embodiments of an intraocular lens and methods of implanting the same into an eye. While particular embodiments of the invention have been described, it is not intended that the invention be limited thereto, as it is intended that the invention be as broad in scope as the art will allow and that the specification be read likewise. Thus, while two particular states of intraocular lenses (fully stressed and fully accommodating) have been disclosed, it will be appreciated that there is a continuum of states of stress that can be fashioned in the inserted lens that would be appropriate for any given state of the ciliary body. In addition, while particular types of materials have been disclosed for the lens, the dissolving material, and a viscoelastic material (where used), it will be understood that other suitable materials can be used. Also, while exemplar pharmacological agents are disclosed for maintaining a state of the ciliary body, it is understood that other agents can be used. Furthermore, while the skirt has been shown comprised of two to four haptics, it is recognized that a single haptic or five or more haptics may be utilized. Moreover, while the restraining struts and shells have been described with respect to skirts comprising haptics, it will be appreciated that the restraining struts and shells can be used with a circular skirt, as described with respect to the preferred embodiments. In addition, while in the second embodiment the optic-haptic junction is stated to preferably have a memory, it is appreciated that other means may be employed to cause the haptics to assume a non-stressed angle configuration relative to optic. For example, an elastic membrane or struts may connect the free ends of the haptics to urge the free ends toward each other and consequently the optic forward. It will therefore be appreciated by those skilled in the art that yet other modifications could be made to the provided invention without deviating from its spirit and scope as claimed.

What is claimed is:

1. An intraocular lens for replacement of a natural crystalline lens within a capsular bag during eye surgery, the intraocular lens to be positioned anterior to the retina when implanted in the eye, said intraocular lens comprising:
   a) an optic portion adapted to focus light;
   b) a peripheral portion including a plurality of haptics about said optic portion, a junction defined between said optic and peripheral portions;

c) biasing means for biasing said optic portion anteriorly relative to said peripheral portion at said junction; and
d) a restraining element including at least one element extending from one haptic across said optic portion and to another haptic, said restraining element operating against said biasing means so as to maintain said optic and peripheral portions in a stressed state of relatively greater planarity than a non-stressed state in which said biasing means urges the optic portion anterior to the peripheral portion,
said restraining element being releasable without an invasive surgical procedure after completion of the eye surgery during which said intraocular lens is implanted,
wherein said restraining element holds said lens at a first total diameter, and when the lens is implanted in the eye, upon release of said restraining element, said biasing means biases said optic portion anteriorly toward the non-stressed state causing said optic portion to be moved anteriorly relative to the retina such that the optic portion is at an increased distance from the retina relative to the stressed state and has a resulting increased optical power, wherein when said optic portion is moved anteriorly in the non-stressed state, said lens assumes a second total diameter smaller than the first total diameter, and wherein the optical power of the lens is adjustable in response to stresses induced by the eye.

2. An intraocular lens according to claim 1, wherein:
said restraining element is chemically dissolvable.

3. An intraocular lens according to claim 1, wherein:
said restraining element is laser releasable.

4. An intraocular lens according to claim 1, wherein:
said restraining element comprises at least one strut.

5. An intraocular lens according to claim 4, wherein:
said at least one strut is arced.

6. An intraocular lens according to claim 1, wherein:
said peripheral portion includes at least one fenestration hole.

7. An intraocular lens according to claim 1, wherein:
said restraining element extends diametrically across said optic portion.

8. An intraocular lens for replacement of a natural crystalline lens within a capsular bag during eye surgery, the intraocular lens to be positioned anterior to the retina when implanted in the eye, said intraocular lens comprising:
a) an optic portion adapted to focus light;
b) a peripheral portion including a plurality of haptics about said optic portion, a junction defined between said optic and peripheral portions;
c) biasing means for inducing a bias along an anterior-posterior axis of the lens to force said optic portion anteriorly relative to said peripheral portion; and
d) a laser releasable restraining element including at least one element extending from one haptic across said optic portion and to another haptic, said restraining element countering said bias of said biasing means to maintain said lens in a relatively planar configuration,
wherein said restraining element holds said lens at a first total diameter, and when the lens is implanted in the eye, upon release of said restraining element, said biasing means biases said optic portion anteriorly relative to said peripheral portion such that when said lens is implanted in the eye said optic portion is caused to be moved anteriorly relative to the retina resulting in increased optical power of the lens with the lens assuming a second total diameter smaller than said first total diameter, and wherein the optical power of the lens is adjustable in response to stresses induced by the eye.

9. An intraocular lens according to claim 8, wherein:
said peripheral portion includes fenestration holes.

10. An intraocular lens according to claim 8, wherein:
said restraining element extends diametrically across said optic portion.

11. An intraocular lens for replacement of a natural crystalline lens within a capsular bag during eye surgery, the intraocular lens to be positioned anterior to the retina when implanted in the eye, said intraocular lens comprising:
a) an optic portion adapted to focus light;
b) a haptic portion including a plurality of haptics about said optic portion;
c) biasing means for biasing said optic portion into an anterior configuration relative to said haptic portion; and
d) a restraining element countering said biasing means to prevent said optic portion from moving into said anterior configuration relative to said haptic portion, said restraining element having a portion extending from a first haptic, at least partially across the optic portion, and to a second haptic, and adapted to be removed after completion of an eye surgery,
wherein said restraining element holds said lens at a first total diameter, and
upon removal of said restraining element, said optic portion is permitted to move anteriorly relative to said haptic portion under the force of the biasing means so that said lens assumes a second total diameter smaller than said first total diameter, and the relative anterior position of said optic portion relative to said haptic portion is adjustable in response to stresses induced by the eye so as to provide an accommodating effect.

12. An intraocular lens according to claim 11 wherein:
said first and second haptics are on diametrically opposing sides of said optic portion.

13. An intraocular lens according to claim 11, wherein:
said restraining element is at least one of bio-resorbable, chemically resorbable, and laser releasable.

14. An intraocular lens according to claim 11, wherein:
said restraining element extends diametrically across said optic portion.

15. An intraocular lens for replacement of a natural crystalline lens within a capsular bag during eye surgery, the intraocular lens to be positioned anterior to the retina when implanted in the eye, said intraocular lens comprising:
a) an optic portion adapted to focus light;
b) a peripheral portion including a plurality of haptics about said optic portion, a junction defined between said optic and peripheral portions, said optic portion biased anteriorly relative to said peripheral portion at said junction; and
c) a restraining element including at least one element extending continuously from a first haptic across said optic portion and to a second haptic, said restraining element operating against said bias so as to maintain said optic and peripheral portions in a stressed state of relatively greater planarity than a non-stressed state in which said optic portion is urged anterior to the peripheral portion,
said restraining element being releasable without an invasive surgical procedure after completion of the eye surgery during which said intraocular lens is implanted,
wherein said restraining element holds said lens at a first total diameter, and when the lens is implanted in the eye, upon release of said restraining element, said optic portion is urged anteriorly relative to said peripheral portion into the non-stressed state causing said optic portion to be moved anteriorly relative to the retina such that the optic portion is at an increased distance from the retina relative to the stressed state and has a resulting increased optical power, wherein when said optic portion is moved anteriorly in the non-stressed state, said lens assumes a second total diameter smaller than the first total diameter, and wherein the optical power of the lens is adjustable in response to stresses induced by the eye.

16. An intraocular lens for replacement of a natural crystalline lens within a capsular bag during eye surgery, the intraocular lens to be positioned anterior to the retina when implanted in the eye, said intraocular lens comprising:
   a) an optic portion adapted to focus light;
   b) a peripheral portion including a plurality of haptics about said optic portion, a junction defined between said optic and peripheral portions, said optic portion biased anteriorly relatively to said peripheral portion at said junction; and
   c) a laser releasable restraining element including at least one element extending continuously across said optic portion from one haptic across said optic portion to another haptic, said restraining element countering said bias between said optic portion and said peripheral portion so as to maintain said lens in a relatively planar configuration,
   wherein said restraining element holds said lens at a first total diameter, and when the lens is implanted in the eye, upon release of said restraining element, the optic portion is urged anteriorly relative to said peripheral portion such that when said lens is implanted in the eye said optic portion is caused to be moved anteriorly relative to the retina resulting in increased optical power of the lens with the lens assuming a second total diameter smaller than said first total diameter, and wherein the optical power of the lens is adjustable in response to stresses induced by the eye.

17. An intraocular lens for replacement of a natural crystalline lens within a capsular bag during eye surgery, the intraocular lens to be positioned anterior to the retina when implanted in the eye, said intraocular lens comprising:
   a) an optic portion adapted to focus light;
   b) a haptic portion including a plurality of haptics about said optic portion, said optic portion biased anteriorly relatively to said haptic portion; and
   c) a restraining element countering said bias to prevent said optic portion from moving into said anterior configuration relative to said haptic portion, said restraining element comprising an element extending continuously across said optic portion from one haptic across said optic portion to another haptic and adapted to be released after completion of an eye surgery,
   wherein said restraining element holds said lens at a first total diameter, and
   upon removal of said restraining element, said optic portion is permitted to move anteriorly relative to said haptic portion under the force of the bias between the optic and haptic portions so that said lens assumes a second total diameter smaller than said first total diameter, and the relative anterior position of said optic portion relative to said haptic portion is adjustable in response to stresses induced by the eye so as to provide an accommodating effect.

18. An intraocular lens for replacement of a natural crystalline lens within a capsular bag during eye surgery, the intraocular lens to be positioned anterior to the retina when implanted in the eye, said intraocular lens comprising:
   a) an optic portion adapted to focus light;
   b) a peripheral portion about said optic portion, a junction defined between said optic and peripheral portions;
   c) biasing means for inducing a bias along an anterior-posterior axis of the lens to force said optic portion anteriorly relative to said peripheral portion; and
   d) a chemically dissolvable restraining element provided to said peripheral portion and extending across said optic portion, said restraining element maintaining said lens in a stressed state of relatively planar configuration against said bias of said biasing means in an environment of the eye until dissolution wherein said optic portion is then able to be urged by said bias toward an accommodating non-stressed state in which said optic portion moves anteriorly relative to said peripheral portion,
   wherein said restraining element holds said lens at a first total diameter and when the lens is implanted in the eye, upon removal of said restraining element, said biasing means biases said optic portion anteriorly toward the non-stressed state causing said optic portion to be moved anteriorly relative to the retina such that the optic portion is at an increased distance from the retina relative to the stressed state and has a resulting increased optical power, and wherein when said optic portion is moved anteriorly in the non-stressed state, said lens assumes a second total diameter smaller than the first total diameter, and wherein the optical power of the lens is adjustable in response to stresses induced by the eye.

19. An intraocular lens according to claim 18, wherein:
said peripheral portion includes a plurality of haptics, and said restraining element includes at least one element extending from one haptic to another haptic.

20. An intraocular lens according to claim 18, wherein:
said peripheral portion includes at least one fenestration hole.

21. An intraocular lens according to claim 18, wherein:
said restraining element extends diametrically across said optic portion.

22. An intraocular lens for replacement of a natural crystalline lens within a capsular bag during eye surgery, the intraocular lens to be positioned anterior to the retina when implanted in the eye, said intraocular lens comprising:
   a) an optic portion adapted to focus light;
   b) a peripheral portion about said optic portion, a junction defined between said optic and peripheral portions, said optic portion biased anteriorly relatively to said peripheral portion at said junction; and
   c) a chemically dissolvable restraining element provided to said peripheral portion and extending across said optic portion and coupled between two locations on said peripheral portion, said restraining element maintaining said lens in a stressed state of relatively planar configuration against said bias in an environment of the eye until dissolution wherein said optic portion is then able to be urged by said bias toward an accommodating non-stressed state in which said optic portion moves anteriorly relative to said peripheral portion,
   wherein said restraining element holds said lens at a first total diameter and when the lens is implanted in the eye, upon removal of said restraining element, said optic portion is urged by said bias anteriorly toward the non-stressed state causing said optic portion to be moved anteriorly relative to the retina such that the optic portion is at an increased distance from the retina relative to the stressed state and has a resulting increased optical power, and wherein when said optic portion is moved anteriorly in the non-stressed state, said lens assumes a second total diameter smaller than the first total diameter, and wherein the optical power of the lens is adjustable in response to stresses induced by the eye.

23. An intraocular lens according to claim 22, wherein:
said peripheral portion includes a plurality of haptics, and a restraining element extends from one haptic across said optic portion and to another haptic.

* * * * *